(12) United States Patent
Chen et al.

(10) Patent No.: US 8,076,153 B2
(45) Date of Patent: *Dec. 13, 2011

(54) METHOD AND APPARATUS FOR MEASURING PH OF LOW ALKALINITY SOLUTIONS

(75) Inventors: Bingzhi Chen, Shanghai (CN); Weiyi Cui, Piscataway, NJ (US); Li Zhang, Shanghai (CN); Caibin Xiao, Harleysville, PA (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/980,791

(22) Filed: Dec. 29, 2010

(65) Prior Publication Data

US 2011/0091985 A1    Apr. 21, 2011

Related U.S. Application Data

(63) Continuation of application No. 11/800,746, filed on May 7, 2007, now Pat. No. 7,883,898.

(51) Int. Cl.
*G01N 31/16* (2006.01)
*G01N 21/00* (2006.01)
(52) U.S. Cl. ............... 436/163; 436/164; 422/82.05; 422/82.09
(58) Field of Classification Search ............... None
See application file for complete search history.

(56) References Cited

U.S. PATENT DOCUMENTS

| | | |
|---|---|---|
| 3,744,975 A | 7/1973 | Mailen |
| 3,998,878 A | 12/1976 | Hearon et al. |
| 4,323,536 A | 4/1982 | Columbus |
| 4,362,386 A | 12/1982 | Matsushita et al. |
| 4,503,156 A | 3/1985 | Yamazato et al. |
| 4,756,884 A | 7/1988 | Hillman et al. |
| 4,857,453 A | 8/1989 | Ullman et al. |
| 4,877,586 A | 10/1989 | Devaney, Jr. et al. |
| 4,894,346 A | 1/1990 | Myers et al. |
| 5,005,572 A | 4/1991 | Raemer et al. |
| 5,032,526 A | 7/1991 | Myers et al. |
| 5,094,752 A | 3/1992 | Davis et al. |
| 5,116,759 A | 5/1992 | Klainer et al. |

(Continued)

FOREIGN PATENT DOCUMENTS

DE    10 2004 013161 A1    10/2005

(Continued)

OTHER PUBLICATIONS

Munoz et al., "Direct Determination of Inorganic Phosphorus in Serum with a Single Reagent", Clinical Chemistry, 1983, vol. 29, No. 2, pp. 372-374.

(Continued)

*Primary Examiner* — Vickie Kim
*Assistant Examiner* — Allison M Gionta
(74) *Attorney, Agent, or Firm* — Wegman, Hessler & Vanderburg (57) ABSTRACT

Systems and methods are described for measuring pH of low alkalinity samples. The present invention provides a sensor array comprising a plurality of pH indicators, each indicator having a different indicator concentration. A calibration function is generated by applying the sensor array to a sample solution having a known pH such that pH responses from each indicator are simultaneously recorded versus indicator concentration for each indicator. Once calibrated, the sensor array is applied to low alkalinity samples having unknown pH. Results from each pH indicator are then compared to the calibration function, and fitting functions are extrapolated to obtain the actual pH of the low alkalinity sample.

12 Claims, 6 Drawing Sheets

U.S. PATENT DOCUMENTS

| | | | |
|---|---|---|---|
| 5,132,345 | A | 7/1992 | Harris et al. |
| 5,234,813 | A | 8/1993 | McGeehan et al. |
| 5,290,705 | A | 3/1994 | Davis |
| 5,300,779 | A | 4/1994 | Hillman et al. |
| 5,342,787 | A | 8/1994 | Bardsley et al. |
| 5,354,692 | A | 10/1994 | Yang et al. |
| 5,389,548 | A | 2/1995 | Hoots et al. |
| 5,478,751 | A | 12/1995 | Oosta et al. |
| 5,482,866 | A | 1/1996 | Denton et al. |
| 5,504,573 | A | 4/1996 | Cheiky-Zelina |
| 5,593,850 | A | 1/1997 | Wetegrove et al. |
| 5,599,913 | A | 2/1997 | Harris et al. |
| 5,645,799 | A | 7/1997 | Shah et al. |
| 5,705,394 | A | 1/1998 | Ananthasubramanian et al. |
| 5,736,405 | A | 4/1998 | Alfano et al. |
| 5,744,794 | A | 4/1998 | Michie et al. |
| 5,747,342 | A | 5/1998 | Zupanovich |
| 5,772,894 | A | 6/1998 | Ward et al. |
| 5,790,627 | A | 8/1998 | Iketaki |
| 5,922,612 | A | 7/1999 | Alder et al. |
| 5,958,788 | A | 9/1999 | Johnson et al. |
| 6,011,882 | A | 1/2000 | Dasgupta et al. |
| 6,030,581 | A | 2/2000 | Virtanen |
| 6,046,052 | A | 4/2000 | Arter et al. |
| 6,051,437 | A | 4/2000 | Luo et al. |
| 6,113,855 | A | 9/2000 | Buechler |
| 6,214,627 | B1 | 4/2001 | Ciota et al. |
| 6,295,506 | B1 | 9/2001 | Heinonen et al. |
| 6,360,585 | B1 | 3/2002 | Potyrailo et al. |
| 6,379,969 | B1 | 4/2002 | Mauze et al. |
| 6,416,652 | B1 | 7/2002 | Lee et al. |
| 6,514,199 | B1 | 2/2003 | Alessandri |
| 6,524,350 | B2 | 2/2003 | Buentello et al. |
| 6,572,902 | B2 | 6/2003 | Abramowitz et al. |
| 6,591,124 | B2 | 7/2003 | Sherman et al. |
| 6,627,177 | B2 | 9/2003 | Singaram et al. |
| 6,641,533 | B2 | 11/2003 | Causey, III et al. |
| 6,645,142 | B2 | 11/2003 | Braig et al. |
| 6,648,820 | B1 | 11/2003 | Sarel |
| 6,676,903 | B2 | 1/2004 | Potyrailo et al. |
| 6,898,531 | B2 | 5/2005 | Sheehan et al. |
| 7,127,356 | B2 | 10/2006 | Nicoli et al. |
| 7,807,473 | B2 | 10/2010 | Potyrailo et al. |
| 2002/0015994 | A1 | 2/2002 | Schellenberger et al. |
| 2002/0040208 | A1 | 4/2002 | Flaherty et al. |
| 2002/0052050 | A1 | 5/2002 | Douglas et al. |
| 2002/0158018 | A1 | 10/2002 | Abramowitz et al. |
| 2003/0022094 | A1 | 1/2003 | Nakamura et al. |
| 2003/0032071 | A1 | 2/2003 | Wang et al. |
| 2003/0035917 | A1 | 2/2003 | Hyman |
| 2003/0157586 | A1 | 8/2003 | Bonde et al. |
| 2003/0217808 | A1 | 11/2003 | Woods et al. |
| 2004/0028566 | A1 | 2/2004 | Ko et al. |
| 2004/0057873 | A1 | 3/2004 | Yerazunis et al. |
| 2004/0191924 | A1 | 9/2004 | Hunter et al. |
| 2005/0111328 | A1 | 5/2005 | Potyrailo et al. |
| 2005/0112358 | A1 | 5/2005 | Potyrailo et al. |
| 2005/0113546 | A1 | 5/2005 | Tao et al. |
| 2005/0176059 | A1 | 8/2005 | Pal et al. |
| 2005/0276769 | A1 | 12/2005 | Herrlein et al. |
| 2006/0009805 | A1 | 1/2006 | Jensen et al. |
| 2006/0029516 | A1 | 2/2006 | Potyrailo |
| 2006/0234384 | A1 | 10/2006 | Kaufman |
| 2007/0092407 | A1 | 4/2007 | Xiao et al. |
| 2007/0092972 | A1 | 4/2007 | Xiao et al. |
| 2007/0092973 | A1 | 4/2007 | Potyrailo et al. |
| 2007/0092975 | A1 | 4/2007 | Potyrailo et al. |
| 2008/0280373 | A1 | 11/2008 | Chen et al. |

FOREIGN PATENT DOCUMENTS

| | | |
|---|---|---|
| EP | 0135298 A2 | 3/1985 |
| EP | 0 902 394 A1 | 3/1999 |
| EP | 0 952 451 A1 | 10/1999 |
| EP | 1 548 423 A1 | 6/2005 |
| JP | 56104248 A | 8/1981 |
| JP | 2004-28775 | 1/2004 |
| JP | 2005-233974 | 9/2005 |
| WO | WO 95/11961 | 5/1995 |
| WO | WO 96/15576 | 5/1996 |
| WO | WO 97/40181 | 10/1997 |
| WO | WO 99/09406 | 2/1999 |
| WO | WO 99/21655 | 5/1999 |
| WO | WO 9958245 | 11/1999 |
| WO | WO 0002845 | 1/2000 |
| WO | WO 0107889 A2 | 2/2001 |
| WO | WO 0138857 A1 | 5/2001 |
| WO | WO 0194921 A2 | 12/2001 |
| WO | WO 0243864 A2 | 6/2002 |
| WO | WO 02071929 A2 | 9/2002 |
| WO | WO 2005066275 A2 | 7/2005 |
| WO | WO 2007050463 A1 | 3/2007 |

OTHER PUBLICATIONS

Barnard et al., "Fiber-Optic Organic Vapor Sensor", Environ. Sci. Technol., 25, No. 7, pp. 1301-1304, 1991.

Yamamoto, "Interaction between Sulphonephthalein Dyes and Quaternary Ammonium Ions in Aqueous Solutions", Analytical Sciences, Jun. 1992, vol. 8, pp. 299-305.

Yang et al., "Chemcial Sensing Using Sol-Gel Derived Planar Waveguides and Indicator Phases", Anal. Chem. 67, No. 8, pp. 1307-1314, Apr. 15, 1995.

Michie et al., "Distributed pH and Water Detection Using Fiber-Optic Sensors and Hydrogels", Journal of Lightwave Technology, vol. 13, No. 7, pp. 1415-1420, Jul. 1995.

Van De Merbel et al., "Sampling and Analytical Strategies in On-Line Bioprocess Monitoring and Control", Journal of Chromatography A, 725, pp. 13-27 1996.

Madaras et al., "Miniaturized Biosensors Employing Electropolymerized Permselective Films and Their Use for Creatinine Assays in Human Serum", Analytical Chemistry, vol. 68, No. 21, Nov. 1, 1996, pp. 3832-3839.

Bownass, et al., "Serially Multiplexed Point Sensor for the Detection of High Humidity in Passive Optical Networks", Optics Letters, vol. 22, No. 5, Mar. 1, 1997, pp. 346-348.

Kosch et al., "Strategies to Design pH Optodes with Luminescence Decay Times in the Microsecond Time Regime", Anal. Chem., 1998, vol. 70, No. 18, Sep. 15, 1998, pp. 3892-3897.

Jackman et al., "Fabricating Large Arrays of Microwells with Arbitrary Dimensions and Filling Them Using Discontinuous Dewetting", Anal. Chem., 70, #11, pp. 2280-2287, 1998.

Potyrailo et al., "Adapting Selected Nucleic Acid Ligands (Aptamers) to Biosensors", Anal. Chem. 70, pp. 3419-3425, 1998.

Potyrailo et al., Optical Waveguide Sensors in Analytical Chemistry: Today's Instrumentation, Apps, and Trends for Future Dev, Fresenius J Anal. Chem., 362, pp. 349-373, 1998.

Delemarche et al., "Microfluidic Networks for Chemical Patterning of Substrates: Design and Application to Bioassays", J. Am. Chem. Soc., 120, No. 3, pp. 500-508, 1998.

Bakker et al., "Ion Sensors: Current Limits and New Trends", Analytica Chimica Acta, 393, pp. 11-18, 1999.

Chierici et al., "Influence of m-cresol purple indicator additions on the pH of seawater samples: correction factors evaluated from a chemical speciation model", Marine Chemistry 65, pp. 281-290, 1999.

Ghauch et al., "Quantitative Measurements of Ammonium, Hydrogenophosphate and Cu(II) by Diffuse Reflectance Spectrometry", Talanta, 48, pp. 385-392 1999.

Michael et al., "A Far-Field-Viewing Sensor for Making Analytical Measurements in Remote Locations", Anal. Chem., 71, No. 14, pp. 2766-2773, 1999.

Byrne, et al., "Digital Imaging as a Detector for Generic Analytical Measurements", Trends in Analytical Chemistry 19, No. 8, pp. 517-522, 2000.

Dickson et al., "Integrated Chem Sensors Based on Carbon Black & Polymer Films Using Standard CMOS Process & Post-Processing", Proc of IEEE Intl Symp, pp. 341-344, May 2000.

Hirayama et al., "Visual and Colorimetric Lithium Ion Sensing Based on Digital Color Analysis", Anal. Chem., 72, No. 3, pp. 465-474, Feb. 1, 2000.

Albert et al., "Cross-Reactive Chemical Sensor Arrays", Chem. Rev., 100, pp. 2595-2626, Jun. 24, 2000.

Rakow et al., "A Colorimetric Sensor Array for Odour Visualization", Nature, 406, pp. 710-713, Aug. 17, 2000.

Cunningham, "Fluidic and Sample Handling in Clinical Chemical Analysis", Analytica Chimica Acta, 429, pp. 1-18, 2001.

Byrne et al., "Digital Imaging as a Detector for Quantitative Colorimetric Analyses", Proc of SPIE, 4205, pp. 267-277, 2001.

Koronczi et al., "Submicron Sensors for Ion Detection Based on Measurement of Luminescence Decay Time", Sensors and Actuators, B 74, 2001, pp. 47-53.

Yao et al., "Spectrophotometric Determination of Freshwater pH Using Bromocresol Purple and Phenol Red", Environ. Sci. Technol., 35, pp. 1197-1201. 2001.

Sequeira et al., "Towards Autonomous Environmental Monitoring Systems", Talanta, 56, pp. 355-363, 2002.

Polerecky et al.,"Optimization of Absorption-Based Optical Chemical Sensors that Employ a Single-Reflection Configuration", Applied Optics, 41, #15, pp. 2879-2887, May 20, 2002.

Suzuki et al, "Ionophore-Based Lithium Ion Film Optode Realizing Muliple Color Variations Utilizing Digital Color Analysis", Anal Chem, 74, No. 22, pp. 5766-5773, Nov. 15, 2002.

Juncker et al., "Autonomous Microfluidic Capillary System", Anal. Chem., 74, pp. 6139-6144, 2002.

Kompany-Zareh et al. "Simple Method for Colorimetric Spot-Test Quantitative Analysis of Fe(III) Using Computer Controlled Hand-Scanner", Anal Chimica Acta, 471, pp. 97-104, 2002.

Stevens et al., "Imaging and Analysis of Immobilized Particle Arrays", Analytical Chemistry, 75, No. 5, pp. 1147-1154, Mar. 1, 2003.

Manzano et al., "Computer Screen Illumination for the Characterization of Colormetric Assays", Sensors and Actuators B, 96, pp. 173-179, 2003.

Bowden et al., "The Determination of Phosphorus in a Microfluidic Manifold Demonstrating Long-Term Reagent Lifetime and Chemical Stability Utilising a Colorimetric Method", Sensors and Actuators B, 90, pp. 170-174, 2003.

Adhikari et al., "Polymers in Sensor Applications", Progress in Polymer Science, vol. 29, pp. 699-766, 2004.

Lau et al., "Solid State Ammonia Sensor Based on Berthelot's Reaction", Sensors and Actuators B, 98, pp. 12-17, 2004.

Lau et al., Novel Fused-LEDs Devices as Optical Sensors for Colorimetric Analysis, Talanta, 63, pp. 167-173, 2004.

Mosley et al., "Spectrophotometric pH measurement in estuaries using thymol blue and m-cresol purple", Marine Chemistry 91 (2004), pp. 175-186.

Zhang et al., "A Colorimetric Sensor Array for Organics in Water", J. Am. Chem. Soc., pp. 11548-11549, 2005.

Freitag, "Sampling Modules, in Biosensors in Analytical Biotechnology", Academic Press, Inc., pp. 1-21, 1996.

Carr-Brion et al., "Sampling Systems for Process Analyzers", Butterworth-Heinemann, Oxford, England, 1996.

Zolotov et al., Chemical Test Methods of Analysis, Wilson & Wilson's Comprehensive Analytical Chemistry, Elsevier, 2002.

The three references listed above are not attached because they are substantially cumulative of the other references listed herein.

METHOD AND APPARATUS FOR MEASURING PH OF LOW ALKALINITY SOLUTIONS

CROSS REFERENCE TO RELATED APPLICATION

This application is a continuation application of and claims the priority benefit of U.S. patent application Ser. No. 11/800,746 filed May 7, 2007.

BACKGROUND OF THE INVENTION

1. Field of Invention

The present invention relates generally to a system for measuring pH, and more particularly relates to an improved method and apparatus for measuring pH of low alkalinity solutions by extrapolating spectrophotometric measurements from a plurality of pH indicator sensors.

2. Description of Related Art

A wide variety of systems and methods have been employed for pH measurement of water systems. For example, a glass electrode is commonly used for pH measurement in both a laboratory and industrial environment. Alternatively, it is known that spectrophotometric techniques may be used for pH measurement. Exemplary systems and methods for pH measurement have been described in U.S. patent application Ser. No. 11/507,689 filed Aug. 22, 2006, which is assigned to the same assignee as the present application, the disclosure of which is hereby incorporated by reference herein.

While the prior art devices and systems have provided useful products, they have not been entirely satisfactory in providing a fast, simple, and accurate measurement of low alkalinity water samples in a relatively simple and user friendly manner. One of the challenges associated with measuring pH of low alkalinity solutions is that perturbation in pH induced by introduction of indicators into the sample solution is not negligible. This is true because indicators themselves are weak acids or bases. Stated another way, the pH of a weakly buffered (i.e., low alkalinity) solution can be severely perturbed due to the fact that the amount of indicator concentration introduced into the sample is significant in relation to the quantity of acid or base in the solution.

Prior art attempts have been made to minimize or correct for indicator induced perturbation in aqueous phase by: (1) adjusting the pH of the indicator stock solution close to the pH of the samples; (2) decreasing the ratio of indicator addition to the sample volume; and (3) observing indicator induced pH perturbations through stepwise indicator additions, and then using linear extrapolation methods to obtain the pH of the sample. Such prior art methods may provide useful results, but they are typically very time consuming and non-user-friendly. Therefore, a strong need remains for an improved method and system that provides a precise, accurate, and fast pH measurement for low alkalinity samples in a relatively cost effective and user-friendly manner.

SUMMARY OF THE INVENTION

One of the challenges associated with measuring pH of low alkalinity solutions is that perturbation in pH values induced by the introduction of indicators into the sample solutions is not negligible. As a result, pH measurements can be severely perturbed due indicator concentrations being introduced into a weakly buffered (i.e., low alkalinity) solution. To meet this challenge, the present invention discloses systems and methods comprising a sensor array comprising a plurality of pH indicators, each indicator having a different indicator concentration. The sensor array is calibrated by applying the sensor array to a sample solution having a known pH. The response from each pH indicator is simultaneously recorded, and a calibration function (i.e., calibration curve) is generated representing the pH response versus indicator concentration for each indicator concentration. Once calibrated, the sensor array may then be applied to low alkalinity sample solutions having unknown pH. Results from the pH values from each pH indicator are compared to the calibration curve, and a fitting function (i.e., fitting equations) representing the pH response from each indicator concentration is generated. Fitting equations are then generated and extrapolated to determine the intercept points (i.e., when indicator concentration is zero) to obtain the original (i.e., actual) pH of the unknown sample.

Other aspects of the present invention relate to the use of such systems and methods, and to exemplary methods for measuring pH of low alkalinity solutions. Further aspects of the present invention and its advantages over the prior art will become apparent upon reading the following detailed description and the appended claims with reference to the accompanying drawings.

DETAILED DESCRIPTION OF INVENTION

The present invention describes systems and methods comprising a polymer film-based sensor array for quickly and accurately measuring pH of low alkalinity solutions, for example low alkalinity water samples. It is known that alkalinity or buffer capacity is one of the basic features of water samples. Alkalinity is a measure of the ability of a solution to neutralize acids. A lower alkalinity means lower capacity to resist the change to pH when an acid is added to the solution.

The concept of the present invention is based on the recognition that in low alkalinity solutions, perturbation of pH induced by introduction of indicators into the sample is not negligible. This is true because indicators themselves are weak acids or bases. As a result, pH of a solution can be severely perturbed due to the fact that the amount of indicator concentration introduced into the sample is significant in relation to the quantity of acid or base present in the weakly buffered (i.e., low alkalinity) solution. This perturbation effect is even more pronounced in pH indicator loaded film.

To meet this challenge, one aspect of the present invention describes an extrapolation process for quickly and accurately measuring pH of low alkalinity samples. The method preferably utilizes, but is not limited to, a sensor array constructed in accordance with U.S. patent application Ser. No. 11/507,689 earlier incorporated by reference herein. Such sensor array is configured to comprise a plurality of indicator portions, each with different indicator concentrations. Once constructed, the sensor array is used to spectrophotometrically measure pH of the sample, whereby each indicator provides a discrete absorbance pH measurement simultaneously. The measured pH values from each indicator portion are plotted versus their respective indicator concentrations, and a fitting function (i.e., fitting equation) representing the measured pH values is extrapolated to determine the intercept points when indicator concentration is zero to obtain the initial pH (i.e., pH real) of the sample. The systems and methods of the present invention provide advantage over known methods because instead of trying to minimize pH perturbations caused by indicator additions, the present invention exploits the relationship between pH perturbations from different indicator concentrations to calibrate the sensor array, thus providing a baseline reference parameter for determining pH measurements from low alkalinity samples having unknown pH.

As disclosed herein, the systems and methods of the present invention are particularly well suited for quickly and accurately determining pH of low alkalinity solutions. Measuring pH of low alkalinity solutions is not trivial due to perturbations induced by the addition of weak acids or base indicators into the solution, especially when the indicator concentration (which is typically either a weak acid or base) is significant in relation to the quantity of acid or base in the sample solution. pH response may be measured by colorimeter, spectrophotometer, or fluorescent spectrometer.

In accordance with an exemplary embodiment of the present invention, a pH sensor array was constructed with a four-film array, although it is understood that more or less films could be used without departing from the scope of the present invention. Each sensor film contained a different pH indicator concentration which will be denoted as $In_1$, $In_2$, $In_3$, and $In_4$ respectively. For purposes of the examples herein, the indicator concentration of each film ranged from about 0.01 to 10%.

The solid films are typically prepared from water-soluble polymers, cellulose acetate, or Poly 2-Hydroxyethyl Methacrylate (pHEMA). The indicators may be colorimetric pH indicators, fluorescent pH indicators, or other suitable pH indicators known or later developed in the art. Colorimetric pH indicators are preferably selected from a group consisting of phenol red, cresol red, m-cresol purple, thymol blue, bromochlorophenol blue W.S., bromocresol green, chlorophenol red, bromocresol purple, bromothymol blue, neutral red, phenolphthalein, o-cresolphthalein, nile blue A, thymolphthalein, bromophenol blue, metacresol purple, malachite green, brilliant green, crystal violet, methyl green, methyl violet 2B, picric acid, naphthol yellow S, metanil yellow, basic fuchsin, phloxine B. methyl yellow, methyl orange, alizarin.

To demonstrate the concepts of the present invention, we carried out a theoretic calculation of pH change (i.e., perturbation) to low alkalinity solutions due to the addition of differing amounts of indicator material into a sample solution. Although the examples disclosed herein are included to demonstrate the broad applicability of the present invention, it should be appreciated by those of skill in the art that the techniques disclosed in the examples herein represent techniques discovered by the inventors, and thus can be considered to constitute exemplary modes for its practice. However, those of skill in the art should, in light of the present disclosure, appreciate that many changes can be made in the specific embodiments which are disclosed and still obtain a like or similar result without departing from the scope of the invention. And the calibration and extrapolation methods disclosed herein may be used to determine pH of low alkalinity samples with pH responses measured by colorimeter, spectrophotometer, or fluorescent spectrometer.

Figure 1:
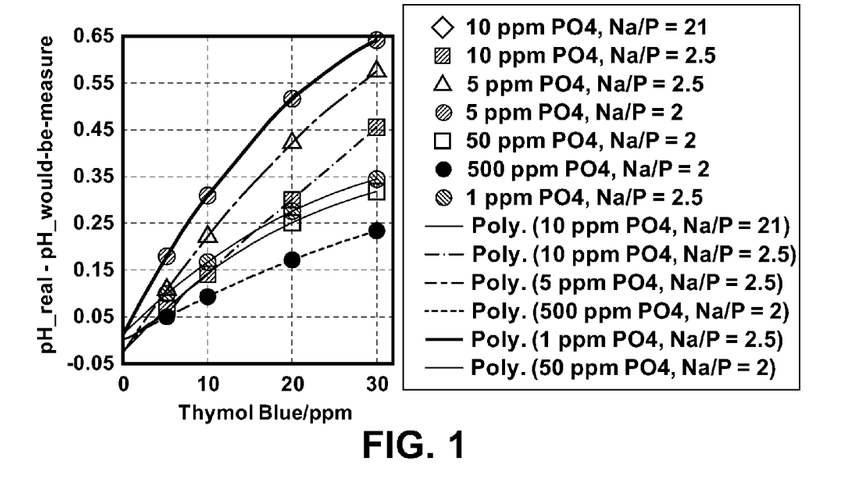
FIG. 1 is a graphical illustration showing changes in pH after introduction of various amounts of thymal blue.

As shown in FIG. 1, a graphical illustration shows how changes in pH are realized after introduction of various amounts of thymal blue into the solution. The results of FIG. 1 indicate that the delta pH (i.e., pH real−pH measured) becomes bigger and bigger with increasing additions of indicator concentration into the solution. This result clearly illustrates that weakly buffered (i.e., low alkalinity) solutions can be severely perturbed by indicator additions.

With continued reference to FIG. 1, theoretic calculation of pH perturbation demonstrates that the lower the alkalinity is, the bigger the delta pH is. Therefore, we can draw the conclusion that with more addition of indicator, and with lower alkalinity, the greater the pH of the solution will be changed or perturbed.

Figure 2:
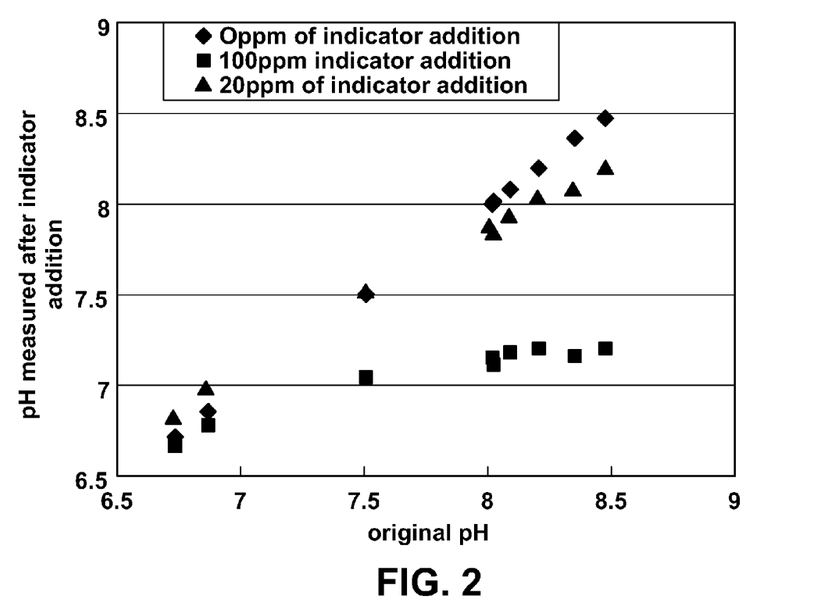
FIG. 2 depicts a series of plots showing pH values of different solutions before and after indicator addition.

To prove this conclusion, we conducted a first experiment in which a series of 100 ppm carbonate buffers were implemented, and the pH value of different solutions was measured before and after indicator additions. Results from this first experiment are shown in FIG. 2. As shown in FIG. 2, a series of plots illustrates pH values of different solutions measured before and after indicator additions. Based on these results, it is apparent that when 20 ppm phenol red (acid form) was added to the solution, the pH measurement slightly decreased. FIG. 2 also illustrates that a gradual decrease of the pH was observed as the amount of phenol red increased from 0 ppm (diamond points) to 100 ppm (square points). When more phenol red 100 ppm was added, the pH was greatly perturbed. As shown by FIG. 2, with 100 ppm phenol red added, solutions with pH higher than about 8.0 became essentially indistinguishable. Based on these results, it became apparent that a correction on delta pH induced by indicator additions could be accounted for to obtain the actual pH (pH real) of the solution.

Accordingly, we conducted a second experiment to show that an extrapolation method may be useful to determine pH. In this second experiment, two 100 ppm carbonate buffers with original pH of 8.12 and 8.53 were chosen. Indicator phenol red which has a pH response range from about 6.8 to 8.2 was used. When an acid form of phenol red was added stepwise to the weakly buffered carbonate solution, a pH meter was used to monitor the pH of the solution.

Figure 3:
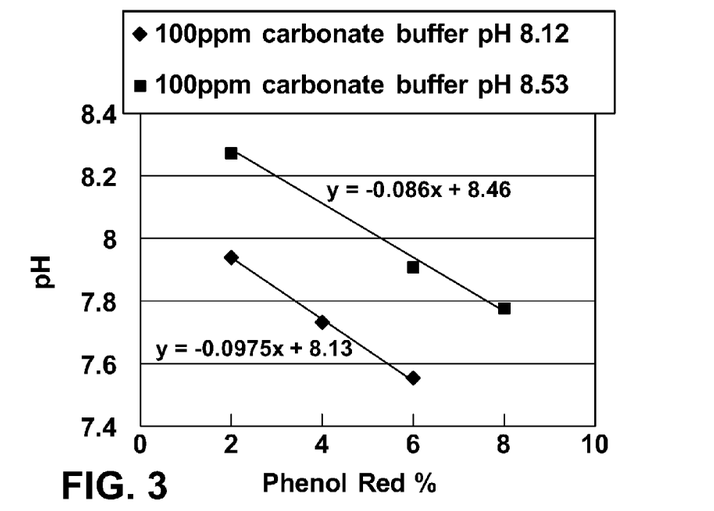
FIG. 3 is a graph illustrating the relationship between pH measured versus the amount of phenol red added.

As shown in FIG. 3, a linear relationship of pH measured to the 100 ppm indicator addition was plotted for each of the 100 ppm carbonate buffers. The linear functions representing pH measured from each indicator type were extrapolated when indicator percentage was zero to obtain the intercept points. As shown in FIG. 3, the intercept points, namely 8.13 and 8.46, represent pH of the solution when indicator concentration is zero. In this way, the intercept points represent the original pH of the solution before indicator additions. It is readily apparent that the intercept points are very close to the initial pH values, i.e., 8.12 and 8.53, of the carbonate buffers, respectively. Consequently, our experiment demonstrates that pH perturbation due to indicator condition is not negligible when alkalinity is very low. Moreover, our experiment demonstrates that the exemplary linear extrapolation technique of the present invention is quite useful to obtain the sample's original pH. The algorithms used in the exemplary extrapolation technique are described in more detail below.

To correct for changes in pH induced by indicator additions, a calibration curve was set up using a synthetic cooling standard solution with high enough alkalinity versus solid pH sensor with a series of indicator concentrations. In this third experiment, the pH of samples was measured with the same solid pH sensor, and the pH measured for each indicator concentration was calculated. The pH measured versus indicator concentration was then plotted and a fitting equation was generated and extrapolated when indicator concentration is zero to obtain the initial pH (i.e., pH real) of the unknown sample.

Figure 4:
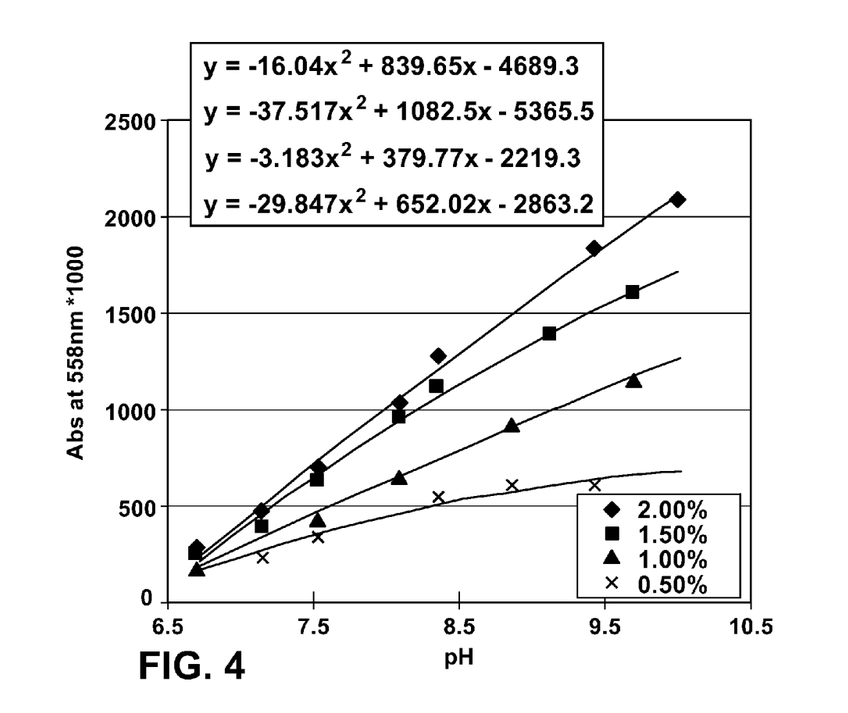
FIG. 4 illustrates calibration curves generated on four distinct indicator concentrations.

As shown in FIG. 4, a calibration curve was generated on four (0.5%, 1.0%, 1.5%, 2.0%) indicator concentrations. The pH value of an unknown sample with low alkalinity (less than 100 ppm) was measured.

Figure 5:
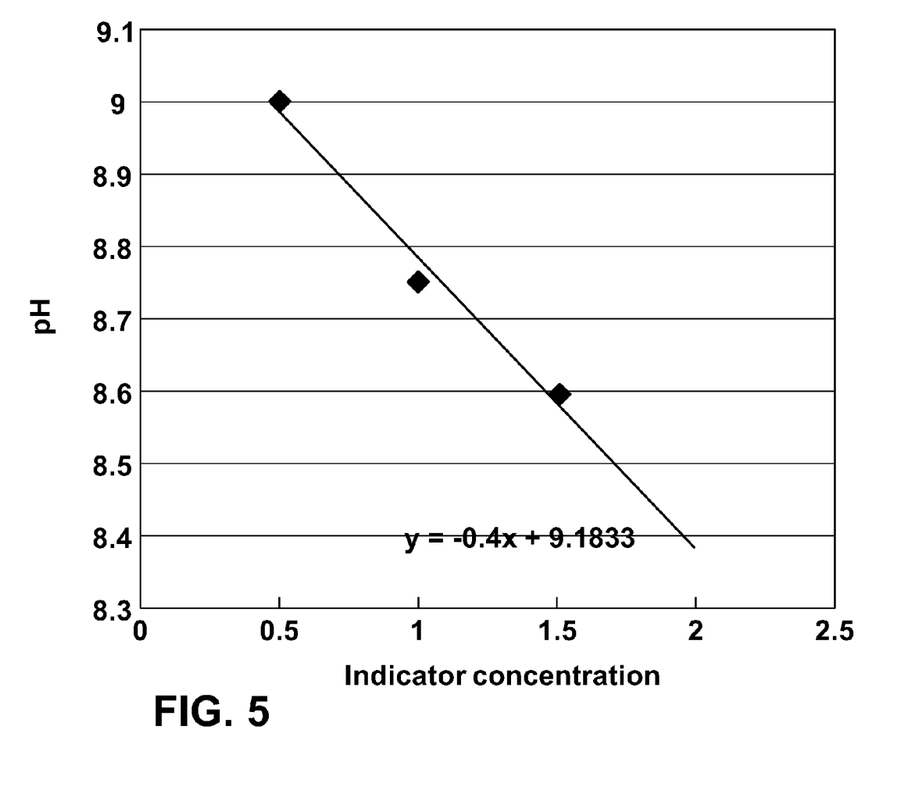
FIG. 5 is a graph illustrating a result from an exemplary linear extrapolation method of the present invention.

FIG. 5 is a graph illustrating results from an exemplary linear extrapolation method of the present invention. As can be seen from FIG. 5, the intercept point of the equation (i.e., when indicator concentration is zero) is 9.18. Since the intercept point represents pH before indicator additions, our extrapolation method demonstrates that the intercept point of 9.18 is a very good approximation to the actual pH value 9.07 measured by a pH meter.

In order to achieve the results illustrated in FIGS. 4 and 5, a pH sensor array was constructed with a four-film array in which each sensor film contained a different pH indicator concentration, as $In_1$, $In_2$, $In_3$, and $In_4$ respectively. Next, an absorbance response was measured for each pH sensor film from a series of pH standard solutions having a fixed and known alkalinity value.

Next, a calibration curve was generated for each pH sensor film from the data measured from the previous second step. The calibration functions are denoted $f_1$, $f_2$, $f_3$, and $f_4$ for purposes of the calculations shown below.

Next, an unknown pH sample was applied to the pH sensor array, and absorbance values measured from each film. For purposes of calculations shown below, these absorbance values are denoted $A_1$, $A_2$, $A_3$, and $A_4$ for films 1, 2, 3, and 4 respectively.

Next, preliminary pH values are calculated for each film from each corresponding calibration equation and absorbance value. For example, pH for films 1-4 are represented as: $pH_1=f_1(A_1)$, $pH_2=f_2(A_2)$, $pH_3=f_3(A_3)$, and $pH_4=f_4(A_4)$, respectively. It is noted that these pH values would all be the same if the alkalinity value of the unknown sample is equal to that of the calibration standard solution. However, $pH_1$, $pH_2$, $pH_3$, and $pH_4$ will all have different values if the alkalinity value of the unknown sample is not equal to that of the calibration standard solution.

In the final step, the actual pH value for the unknown sample is calculated from the preliminary pH values $pH_1$, $pH_2$, $pH_3$, and $pH_4$ based on the extrapolation algorithm given below:

$$pH_{sample} = \begin{vmatrix} \Sigma(In_i^2) & \Sigma(In_i * pH_i) \\ \Sigma In_i & \Sigma pH_i \end{vmatrix} \Bigg/ \begin{vmatrix} \Sigma(In_i^2) & \Sigma In_i \\ \Sigma In_i & N \end{vmatrix} \quad \text{Equation 1}$$

where:
i is the film index;
$In_i$ stands for the indicator concentration in the $i^{th}$ film;
$pH_i$ is the apparent pH value calculated from absorbance of the $i^{th}$ film and the corresponding calibration equation $f_i$;
and N is number of pH films.

FIG. 5 is a graphic illustration of the exemplary extrapolation algorithm. Calculations for the results shown in FIG. 5 and the corresponding mathematic procedure are shown below:

$N=4, i=1, 2, 3,$ and $4$   Equation 2:

$\Sigma(In_i)^2 = 2.0^2 + 1.5^2 + 1.0^2 + 0.5^2 = 7.5$   Equation 3:

$\Sigma pH_i = 8.38 + 8.60 + 8.75 + 9.00 = 34.73$   Equation 4:

$\Sigma In_i = 2.0 + 1.5 + 1.0 + 0.5 = 5.0$   Equation 5:

$\Sigma In_i \cdot pH_i = 2.0 \times 8.38 + 1.5 \times 8.60 + 1.0 \times 8.75 + 0.5 \times 9.00 = 42.91$   Equation 6:

$pH\ sample = (34.73 \times 7.5 - 5.0 \times 42.9)/(7.5 \times 4 - 5.0 \times 5.0) = 9.18$   Equation 7:

Based on the results describe above, the present invention thus provides a system for directly measuring the pH of low alkalinity samples by providing a sensor array having a plurality of indicator concentrations, and calibrating the pH measured of an unknown sample to the calibration curve generated from a known sample to obtain the pH of the unknown sample. In accordance with the present invention, these measurements are recorded simultaneously in a timely manner to avoid the tedious and lengthy measurements and calculations involved with stepwise indicator additions. As an example, an exemplary solid film sensor of the present invention demonstrated a rapid response to the target, with results being obtained within about five minutes for in situ (on field) tests.

As described herein, the systems and methods of the present invention incorporate a solid polymer-based pH sensor film array comprising a series of different indicator concentrations. Once constructed, the sensor array is applied to a sample solution containing a known pH and alkalinity. The pH response from each indicator concentration is simultaneously measured and recorded. Next, a calibration function (i.e., calibration curve) is generated by plotting the pH measured versus each indicator concentration. The calibration curve thus represents a plot of the pH measured versus indicator concentration. Next, a fitting function (i.e., fitting equation) representing each pH measurement is generated. The fitting equation is extrapolated to determine the intercept points when indicator concentration is zero, thus obtaining an accurate indication of the original pH of the sample before indicator additions. In this way, the calibration curve represents a baseline reference function which can be used to calibrate the discrete results from each indicator portion to quickly and easily exploit the perturbation of pH from different indicator additions so as to extrapolate the pH of low alkalinity samples.

Figure 6:
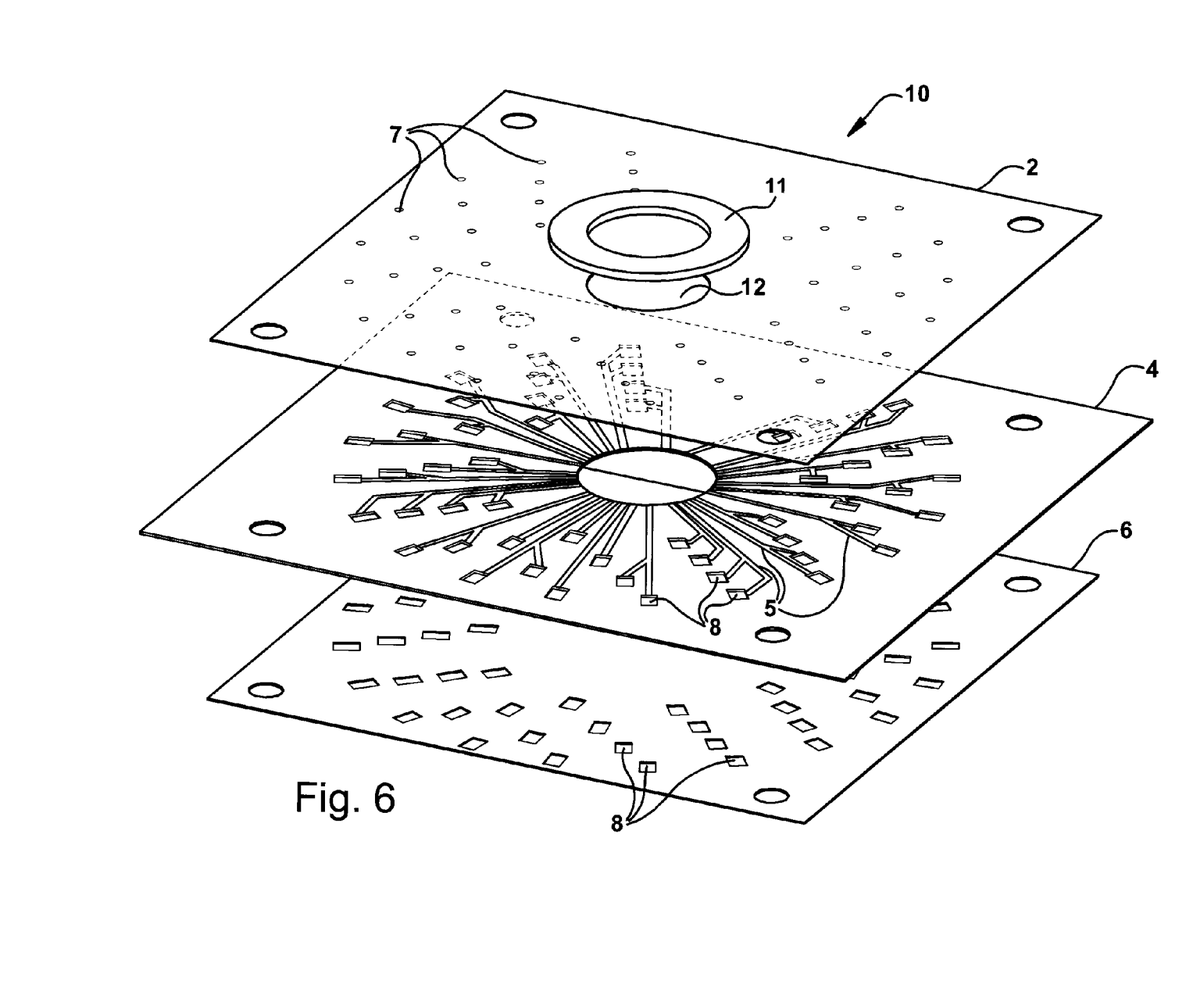
FIG. 6 depicts a pH sensor array in accordance with an exemplary embodiment of the present invention.

FIG. 6 depicts a pH sensor array in accordance with an exemplary embodiment of this invention. The array 10 transports a controlled amount of a liquid sample, in metered quantities, to multiple reservoirs 8 in order to effect a chemical reaction between the sample fluid and the sensor elements (not shown) connected to the reservoirs 8. As shown in FIG. 6, the array 10 comprises a top cover layer 2, a middle channel layer 4, a bottom sampler-substrate binding (i.e., gasket) layer 6, a fluid entry port 12, and an associated plastic entry port wall ring 11. A plurality of grooves or channels 5 are formed on the channel layer 4 for directing the sample fluid from the fluid entry port 12 to the reservoirs 8. A plurality of channels is formed when the cover layer 2 is bound to the channel layer 4. A series of vent holes 7 are added to assure complete fluid flow through the channel system. Due to the capillary force driving the fluid through the channels 5, no pumps and valves are required to deliver a given amount of liquid sample or reagent from the sample entry port 12 to the multiple reservoirs 8 within a predefined sequence.

Figure 7:
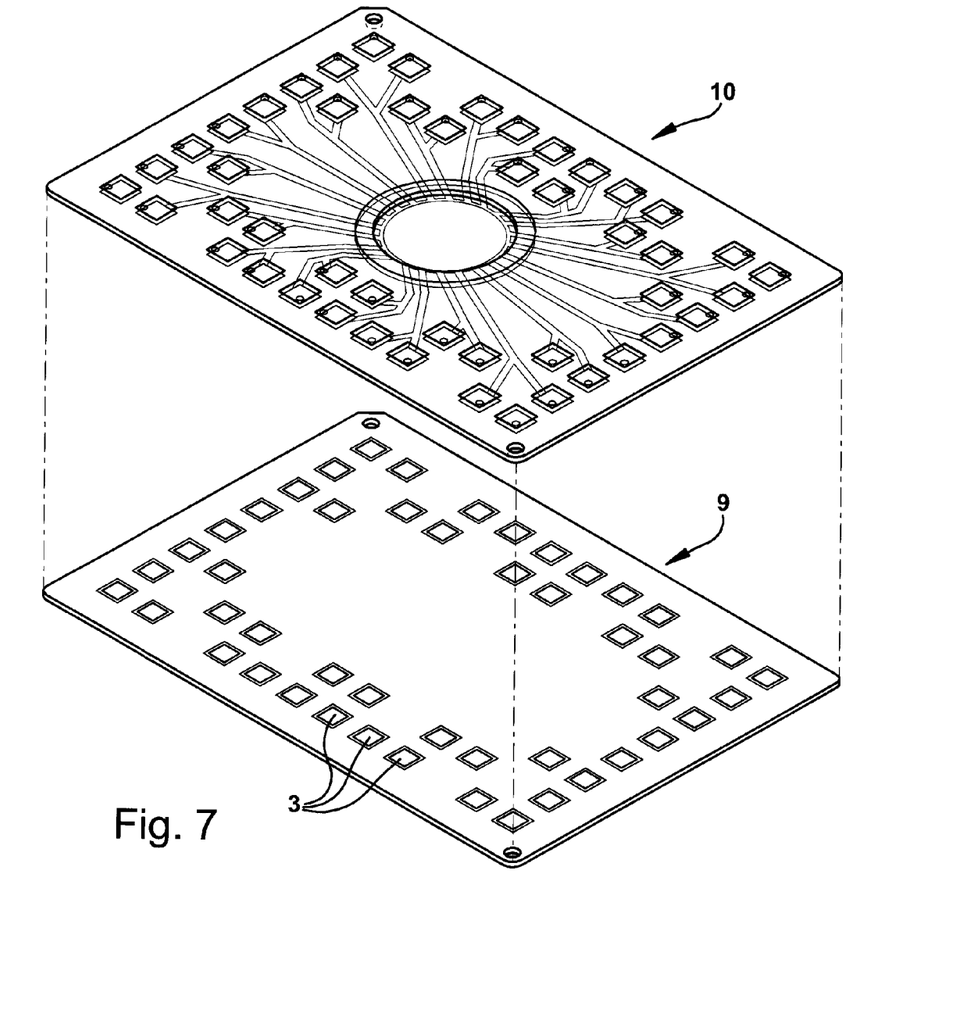
FIG. 7 depicts a single use or disposable test array card in accordance with an exemplary embodiment of the present invention.

FIG. 7 illustrates a single-use or disposable test array card 9, also referred to as a disk or substrate, comprising diverse chemically or physically responsive sensor films 3 in accordance with an exemplary embodiment of the present invention. The sensor films 3 can be grouped into chemical or physically similar sets of one or more films depending on the desired fidelity of a sensor response through the use of outlier elimination or statistically processing of the individual film responses.

Figure 8:
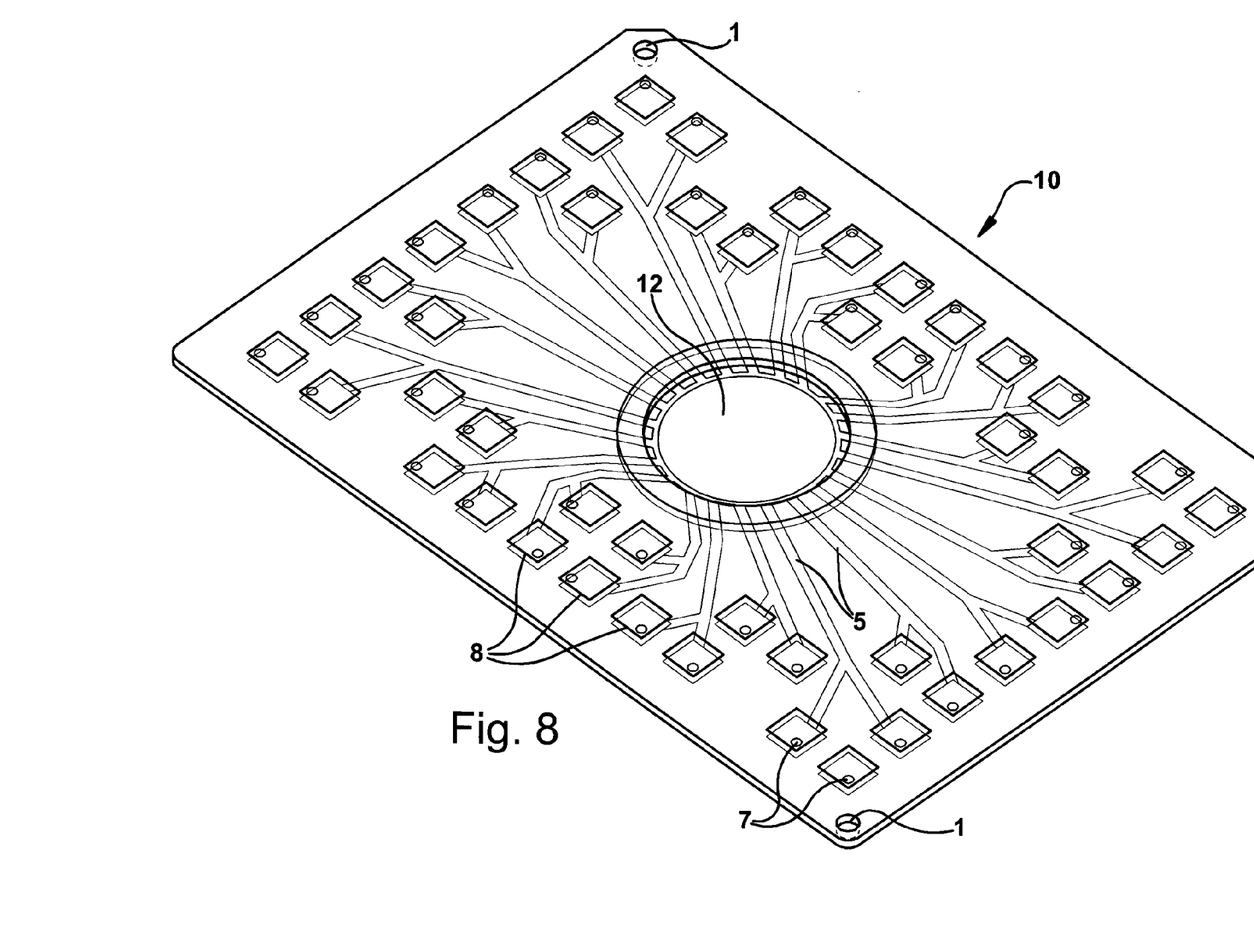
FIG. 8 depicts a fluidic delivery device that can be used with the test array card of FIG. 7.

FIG. 8 illustrates a fluidic delivery device 10 that can be aligned and assembled to the test array card 9 using the locating holes 1. The delivery device 10 transports a controlled amount of a liquid sample injected at the entry port 12, in metered quantities, to an array of reservoirs 8 through channels 5 radiating out of the entry port 12 to the reservoirs 8 in order to effect a chemical reaction between the sample fluid and the sensor element 3 connected to the cell. In addition, the fluidic delivery device provides four sidewalls and the roof of the reservoirs with the test array card 9 providing the bottom floor. The roof of the reservoirs comprises a film that has circular vent holes 7 that vent air out of the reservoirs as they are filled with sample liquid. The vent hole material, diameter and depth are optimized to regulate the effective venting of air and containment of sample fluid within the controlled dimensions of walls of the reservoirs 8.

While the disclosure has been illustrated and described in typical exemplary embodiments, it is not intended to be limited to the details shown, since various modifications and substitutions can be made without departing in any way from the scope and spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A method for measuring pH of a low alkalinity sample solution, comprising the steps of:
    providing a pH sensor array having a plurality of pH indicator films, each said pH indicator film having a different indicator concentration;
    applying said sensor array to a series of pH standard solutions having fixed and known pH and alkalinity values;
    simultaneously measuring a pH response for each pH indicator film of said sensor array;
    generating a calibration equation for each pH indicator film that provides the apparent pH as a function of said measured pH response, said calibration equations are generated using said measured pH responses for each pH indicator film from said series of pH standard solutions;
    applying said sensor array to a low alkalinity sample solution having an unknown pH and an alkalinity of less than 100 ppm;
    calculating apparent pH values for each film from each corresponding calibration equation and said measured pH response; and
    calculating the actual pH value for the low alkalinity sample solution using extrapolation.

2. The method of claim 1, wherein said calculating apparent pH values step comprises using the equation:

$$pH_i = f_i(A_i)$$

where:
  i is the pH indicator film index,
  $f_i$ is the calibration equation that provides the apparent pH value as a function of the measured pH response for the $i^{th}$ pH indicator film,
  $A_i$ is the measured pH response for the $i^{th}$ pH indicator film,
  $pH_i$ is the apparent pH value calculated from the measured pH response of the $i^{th}$ pH indicator film and the corresponding calibration equation.

3. The method of claim 2, wherein said extrapolating step comprises using said apparent pH values to generate an intercept point.

4. The method of claim 3, wherein said extrapolation step comprises using the extrapolation equation:

$$pH_{sample} = \begin{vmatrix} \Sigma(In_i^2) & \Sigma(In_i * pH_i) \\ \Sigma In_i & \Sigma pH_i \end{vmatrix} \Bigg/ \begin{vmatrix} \Sigma(In_i^2) & \Sigma In_i \\ \Sigma In_i & N \end{vmatrix}$$

where:
  i is the index corresponding to each pH indicator;
  $In_i$ is the indicator concentration of the $i^{th}$ indicator;
  $pH_i$ the apparent pH value calculated from the measured pH response of the $i^{th}$ pH indicator film and the corresponding calibration equation; and
  N is number of pH indicators.

5. The method of claim 1, wherein said indicators are solid polymer based, pH indicator-containing films.

6. The method of claim 5, wherein said indicators are colorimetric pH indicators or fluorescent pH indicators.

7. The method of claim 6, wherein said colorimetric pH indicators are selected from the group consisting of phenol red, cresol red, m-cresol purple, thymol blue, bromochlorophenol blue W.S., bromocresol green, chlorophenol red, bromocresol purple, bromothymol blue, neutral red, phenolphthalein, o-cresolphthalein, nile blue A, thymolphthalein, bromophenol blue, metacresol purple, malachite green, brilliant green, crystal violet, methyl green, methyl violet 2B, picric acid, naphthol yellow S, metanil yellow, basic fuchsin, phloxine B. methyl yellow, methyl orange, alizarin.

8. The method of claim 5, wherein said solid films are prepared from water-soluble polymers.

9. The method of claim 5, wherein said solid films are prepared from Poly 2-Hydroxyethyl Methacrylate (pHEMA) or cellulose acetate.

10. The method of claim 5, wherein said sensor array comprises at least four pH indicators having concentrations on the order of about 0.01% to 10%.

11. The method of claim 1, further comprising the step of generating graphical representations of said calibration equations and apparent pH values.

12. The method of claim 1, wherein said pH response is measured by colorimeter, spectrophotometer, or fluorescent spectrometer.

* * * * *